(12) United States Patent
Iddan et al.

(10) Patent No.: US 9,432,562 B2
(45) Date of Patent: *Aug. 30, 2016

(54) DEVICE AND SYSTEM FOR IN VIVO IMAGING

(75) Inventors: Gavriel J. Iddan, Haifa (IL); Dov Avni, Haifa (IL); Arkady Glukhovsky, Nesher (IL); Gavriel Meron, Petach Tikva (IL)

(73) Assignee: GIVEN IMAGING LTD., Yoqneam (IL)

( * ) Notice: Subject to any disclaimer, the term of this patent is extended or adjusted under 35 U.S.C. 154(b) by 1895 days.

This patent is subject to a terminal disclaimer.

(21) Appl. No.: 11/337,570

(22) Filed: Jan. 24, 2006

(65) Prior Publication Data

US 2006/0132599 A1    Jun. 22, 2006

Related U.S. Application Data

(63) Continuation of application No. 09/800,470, filed on Mar. 8, 2001, now Pat. No. 7,009,634, and a continuation of application No. 11/295,491, filed on Dec. 7, 2005.

(60) Provisional application No. 60/187,883, filed on Mar. 8, 2000.

(51) Int. Cl.
*A61B 1/04* (2006.01)
*H04N 5/225* (2006.01)
(Continued)

(52) U.S. Cl.
CPC ........... *H04N 5/2256* (2013.01); *A61B 1/0016* (2013.01); *A61B 1/00036* (2013.01); *A61B 1/041* (2013.01); *A61B 1/0607* (2013.01); *A61B 1/0676* (2013.01); *A61B 1/0684* (2013.01); *A61B 5/0031* (2013.01); *A61B 5/073* (2013.01); *A61B 5/14539* (2013.01); *H04L 25/03866* (2013.01); *H04N 5/2251* (2013.01); *H04N 5/2252* (2013.01); *H04N 5/23203* (2013.01); *H04N 7/185* (2013.01); *A61B 1/00032* (2013.01); *A61B 1/2733* (2013.01);
(Continued)

(58) Field of Classification Search
CPC .......... A61B 1/00016; A61B 1/00032; A61B 1/00036; H04L 25/03866; H04N 2005/2255; H04N 5/2252; H04N 5/2256
See application file for complete search history.

(56) References Cited

U.S. PATENT DOCUMENTS 3,683,389 A    8/1972  Hollis
3,796,221 A    3/1974  Hagfors
(Continued)

FOREIGN PATENT DOCUMENTS

DE    34 40 177    5/1986
EP    0 667 115    8/1995
(Continued)

OTHER PUBLICATIONS

U.S. Appl. No. 10/200,548, filed Jul. 23, 2002, Glukhovsky, et al.
(Continued)

*Primary Examiner* — Nhon Diep
(74) *Attorney, Agent, or Firm* — Pearl Cohen Zedek Latzer Baratz LLP

(57) ABSTRACT

The present invention provides a system and method for obtaining in vivo images. The system contains an imaging system and a transmitter for transmitting signals from a camera to a receiving system located outside a patient.

19 Claims, 5 Drawing Sheets

(51) Int. Cl.
*A61B 1/00* (2006.01)
*A61B 1/06* (2006.01)
*A61B 5/00* (2006.01)
*A61B 5/07* (2006.01)
*A61B 5/145* (2006.01)
*H04L 25/03* (2006.01)
*H04N 5/232* (2006.01)
*H04N 7/18* (2006.01)
*A61B 1/273* (2006.01)
*A61B 1/31* (2006.01)

(52) U.S. Cl.
CPC ............... *A61B 1/2736* (2013.01); *A61B 1/31* (2013.01); *A61B 2560/0209* (2013.01); *H04N 2005/2255* (2013.01)

(56) References Cited

U.S. PATENT DOCUMENTS

| | | |
|---|---|---|
| 3,931,636 A | 1/1976 | Schneider |
| 3,971,362 A | 7/1976 | Pope et al. |
| 3,984,628 A | 10/1976 | Sharp |
| 4,273,431 A | 6/1981 | Farmer et al. |
| 4,278,077 A | 7/1981 | Mizumoto |
| 4,414,979 A | 11/1983 | Hirshorn et al. |
| 4,416,283 A | 11/1983 | Slocum |
| 4,428,005 A | 1/1984 | Kubo |
| 4,532,918 A | 8/1985 | Wheeler |
| 4,539,603 A | 9/1985 | Takeuchi et al. |
| 4,646,724 A | 3/1987 | Sato et al. |
| 4,689,621 A | 8/1987 | Kleinberg |
| 4,741,327 A | 5/1988 | Yabe |
| 4,786,982 A | 11/1988 | Wakahara et al. |
| 4,841,291 A | 6/1989 | Swix et al. |
| 4,844,076 A | 7/1989 | Lesho et al. |
| 4,858,012 A | 8/1989 | Hino et al. |
| 4,884,133 A | 11/1989 | Kanno et al. |
| 5,010,412 A | 4/1991 | Garriss |
| 5,187,572 A | 2/1993 | Nakamura et al. |
| 5,202,961 A | 4/1993 | Mills et al. |
| 5,203,779 A | 4/1993 | Muller et al. |
| 5,267,033 A | 11/1993 | Hoshino |
| 5,279,607 A | 1/1994 | Schentag et al. |
| 5,351,161 A | 9/1994 | MacKay et al. |
| 5,355,450 A | 10/1994 | Garmon et al. |
| 5,365,287 A | 11/1994 | Vollmer et al. |
| 5,423,312 A * | 6/1995 | Siegmund et al. ............ 600/109 |
| 5,486,861 A | 1/1996 | Miyamoto et al. |
| 5,495,114 A | 2/1996 | Adair |
| 5,519,828 A | 5/1996 | Rayner |
| 5,604,531 A | 2/1997 | Iddan et al. |
| 5,643,175 A | 7/1997 | Adair |
| 5,678,568 A | 10/1997 | Uchikubo et al. |
| 5,699,121 A | 12/1997 | Zakhor et al. |
| 5,734,418 A | 3/1998 | Danna |
| 5,749,367 A | 5/1998 | Gamlyn et al. |
| 5,809,161 A | 9/1998 | Auty et al. |
| 5,817,015 A | 10/1998 | Adair et al. |
| 5,819,736 A | 10/1998 | Avny et al. |
| 5,833,603 A | 11/1998 | Kovacs et al. |
| 5,875,280 A | 2/1999 | Takaiwa et al. |
| 5,886,353 A | 3/1999 | Spivey et al. |
| 5,909,026 A | 6/1999 | Zhou et al. |
| 5,929,901 A | 7/1999 | Adair et al. |
| 5,986,693 A | 11/1999 | Adair et al. |
| 5,993,378 A | 11/1999 | Lemelson |
| 5,999,091 A | 12/1999 | Wortham |
| 6,043,839 A | 3/2000 | Adair et al. |
| 6,058,114 A | 5/2000 | Sethuram et al. |
| 6,106,457 A | 8/2000 | Perkins et al. |
| 6,117,529 A | 9/2000 | Leising et al. |
| 6,240,312 B1 | 5/2001 | Alfano et al. |
| 6,277,064 B1 | 8/2001 | Yoon |
| 6,300,946 B1 | 10/2001 | Lincke et al. |
| 6,310,642 B1 | 10/2001 | Adair et al. |
| 6,324,418 B1 | 11/2001 | Crowley et al. |
| 6,328,212 B1 | 12/2001 | Metlitasky et al. |
| 6,351,606 B1 | 2/2002 | Yamazaki |
| 6,371,927 B1 | 4/2002 | Brune et al. |
| 6,393,431 B1 | 5/2002 | Salvati et al. |
| 6,396,438 B1 | 5/2002 | Seal |
| 6,594,036 B1 | 7/2003 | Wong et al. |
| 6,603,103 B1 | 8/2003 | Ulrich et al. |
| 6,607,301 B1 | 8/2003 | Glukhovsky et al. |
| 6,636,263 B2 | 10/2003 | Oda |
| 6,667,765 B1 | 12/2003 | Tanaka |
| 6,690,412 B1 | 2/2004 | Higo |
| 6,709,387 B1 | 3/2004 | Glukhovsky et al. |
| 6,738,663 B2 | 5/2004 | Shroeppel et al. |
| 6,764,440 B2 | 7/2004 | Iddan et al. |
| 6,865,718 B2 | 3/2005 | Levi Montalcini |
| 7,009,634 B2 | 3/2006 | Iddan et al. |
| 7,039,453 B2 | 5/2006 | Mullick et al. |
| 7,295,226 B1 | 11/2007 | Meron et al. |
| 2001/0019364 A1 | 9/2001 | Kawahara |
| 2001/0035902 A1 | 11/2001 | Iddan et al. |
| 2002/0042562 A1 | 4/2002 | Meron et al. |
| 2002/0093484 A1 | 7/2002 | Skala et al. |
| 2002/0103417 A1 | 8/2002 | Gazdzinski |
| 2002/0171669 A1 | 11/2002 | Meron et al. |
| 2003/0028978 A1 | 2/2003 | Glukhovsky |
| 2003/0117491 A1 | 6/2003 | Avni et al. |
| 2003/0174208 A1 | 9/2003 | Glukhovsky et al. |
| 2006/0082648 A1 | 4/2006 | Iddan |
| 2006/0132599 A1 | 6/2006 | Iddan et al. |
| 2006/0158512 A1 | 7/2006 | Iddan et al. |
| 2006/0192889 A1 | 8/2006 | Iddan |
| 2008/0033243 A1 | 2/2008 | Meron et al. |

FOREIGN PATENT DOCUMENTS

| | | |
|---|---|---|
| EP | 0 677 272 | 10/1995 |
| EP | 0 941 691 | 9/1999 |
| EP | 0 977 278 | 2/2000 |
| EP | 1 779 777 | 5/2007 |
| JP | 57-458333 | 3/1982 |
| JP | 5745833 | 3/1982 |
| JP | 05015515 | 2/1991 |
| JP | 3289779 | 12/1991 |
| JP | 4022325 | 1/1992 |
| JP | 04-109927 | 4/1992 |
| JP | 4109927 | 4/1992 |
| JP | 04-144533 | 5/1992 |
| JP | 4-144533 | 5/1992 |
| JP | 4180736 | 6/1992 |
| JP | 5015515 | 1/1993 |
| JP | 05-200015 | 8/1993 |
| JP | 6285044 | 10/1994 |
| JP | 08-248326 | 9/1996 |
| JP | 09-327447 | 12/1997 |
| JP | 10-216085 | 8/1998 |
| JP | 11-009548 | 1/1999 |
| JP | 11-076151 | 3/1999 |
| JP | 11-225996 | 8/1999 |
| JP | 11225996 | 8/1999 |
| JP | 3017770 | 12/1999 |
| JP | 2001-025004 | 1/2001 |
| JP | 2001-224553 | 8/2001 |
| KR | 99-68036 | 8/1999 |
| WO | WO 92/21307 | 12/1992 |
| WO | WO 97/33513 | 9/1997 |
| WO | WO 98/11816 | 3/1998 |
| WO | WO 99/21359 | 4/1999 |
| WO | WO 00/22975 | 4/2000 |
| WO | WO 00/76391 | 12/2000 |
| WO | WO 01/08548 | 2/2001 |
| WO | WO 01/35813 | 5/2001 |
| WO | WO 01/50941 | 7/2001 |
| WO | WO 01/65995 | 9/2001 |
| WO | WO 01/87377 | 11/2001 |
| WO | WO 02/080376 | 10/2002 |
| WO | WO 02/094337 | 11/2002 |
| WO | WO 02/095351 | 11/2002 |
| WO | WO 03/003706 | 1/2003 |

(56) References Cited

FOREIGN PATENT DOCUMENTS

| WO | WO 03/009739 | 2/2003 |
|---|---|---|
| WO | WO 03/011103 | 2/2003 |
| WO | WO 03/028224 | 4/2003 |
| WO | WO 2004/082472 | 9/2004 |

OTHER PUBLICATIONS

U.S. Appl. No. 10/724,109, filed Dec. 1, 2003, Glukhovsky, et al.
International Search Report—PCT application No. PCT/IL01/00215, Dated May 7, 2002.
The Radio Pill, Rowlands, et al. British Communications and Electronics, Aug. 1960, pp. 598-601.
Video Camera to "TAKE"—RF System Lab.
Wellesley company sends body monitors into space—Crum, Apr. 1998.
Wireless transmission of a color television moving image from the stomach using a miniature CCD camera, light source and microwave transmitter. Swain CP, Gong F, Mills TN. Gastrointest Endosc 1997: 45:AB40.
BBC News Online—Pill camera to "broadcast from the gut", Feb. 21, 2000, www.news.bbc.co.uk.
Manual of Photogrammetry. Thompson (Ed.). Third Edition. vol. Two, American Society of Photogrammetry. 1996.
www.jason.net—Tiny cam © 2000.
www.pedinc.com—Personal Electronic Devices, Inc. © 1997.
U.S. Appl. No. 11/295,491, filed Dec. 7, 2005, Iddan, Gavriel J.
U.S. Appl. No. 11/976,794, filed Oct. 29, 2007, Iddan, Gavriel J.
U.S. Appl. No. 11/415,171, filed May 2, 2006, Iddan, Gavriel J.
Office Action, U.S. Appl. No. 11/295,491 dated Aug. 19, 2009.
Glukhovsky et al., "Wireless-Capsule diagnostic endoscopy for recurrent small-bowel bleeding", New England Journal of Medicine, Jan. 18, 2001, vol. 344, Nr. 3, p. 223-233.
Appleyard et al., "A Randomized Trial Comparing wireless capsule endoscopy with push endoscopy for the detection of small-bowel Lesions", Gastroenterology, Dec. 2000, vol. 119, p. 1431-1438.
Gong et al., "Wireless endoscopy", Gastrointestinal endoscopy, Jun. 2000, vol. 51, Nr. 6, p. 725-729.
Swain et al., Wireless capsule endoscopy of the small-bowel, Conference Proceedings from 'Biomonitoring and Endoscopy Technologies', Jul. 5-6, 2000, Amsterdam, Proceedings of SPIE—The International Society for Optical Engineering, vol. 4158.
Fossum, "CMOS image sensors: electronic camera-on-a-chip", IEEE Transactions on Electron Devices, vol. 44, Nr. 10, p. 1689-1698.
European Office Action of Application No. 06 010 954.3 issued on Jan. 14, 2009.
European Office Action of Application No. 07 001 478.2 issued on Dec. 30, 2008.
Office Action, issued Jun. 21, 2010, for U.S. Appl. No. 11/363,185.
Japanese Office Action, issued May 17, 2010, for Japanese Application No. 2001-564653.
U.S. Appl. No. 11/094,831, filed Mar. 31, 2005, Bettesh et al.
U.S. Appl. No. 11/337,570, filed Jan. 24, 2006, Iddan et al.
U.S. Appl. No. 11/363,185, filed Feb. 28, 2006, Iddan et al.
"A Low-Power Miniature Transmitter Using a Low-Loss Silicon Platform for Biotelemetry" Ziaie B et al 19 Annual International Conference of the IEEE Engineering in Medicine and Biology Society. vol. 5, 1994 pp. 2221-2224.
Australian Office Action, Application No. 2005-244523 dated Feb. 6, 2007.
European Search Report Application No. 07001478 completed Apr. 2, 2007.
European Search Report Application No. 07001479 dated Apr. 10, 2007.
"Integrated RF Transmitter Based on SAW Oscillator" Neuberger A et al. 23rd European Southampton, UK Sep. 16-18, 1997, Piscataway, NJ USA IEEE, pp. 344-347.
Japanese Office Action, Application No. 2005-156061 dated Nov. 2, 2005.
Japanese Office Action, Application No. 2005-156060 mailed Aug. 29, 2005.
Japanese Office Action, Application No. 2001-564653 dated Jun. 12, 2007.
Korean Office Action, Application No. 2006-7019809 dated May 28, 2007.
Supplementary European Search Report Application No. 01912088 dated Mar. 21, 2006.
Supplementary European Search Report Application No. 06010954.3 dated Aug. 3, 2006.
Supplementary European Search Report Application No. 06010954.3 dated Nov. 7, 2006.
Office Action, U.S. Appl. No. 09/800,470 dated Sep. 27, 2004.
Office Action, U.S. Appl. No. 09/800,470 dated Aug. 4, 2005.
Translated Japan Office Action of Application No. 2001-564563, dated Feb. 14, 2008.
U.S. Appl. No. 60/187,883, filed Mar. 8, 2000, Meron.
U.S. Appl. No. 60/251,493, filed Dec. 7, 2000, Skala.
U.S. Appl. No. 60/307,603, filed Jul. 26, 2001, Avni.
United States Office Action of U.S. Appl. No. 10/130,326 dated Nov. 4, 2005.
United States Office Action of U.S. Appl. No. 10/130,326 dated Aug. 11, 2006.
United States Office Action of U.S. Appl. No. 10/004,270 dated Jun. 3, 2004.
United States Office Action of U.S. Appl. No. 10/004,270 dated May 20, 2005.
United States Office Action of U.S. Appl. No. 10/004,270 dated Feb. 23, 2006.
United States Office Action of U.S. Appl. No. 10/004,270 dated Aug. 1, 2006.
Japanese Office Action of Application No. 2001-564653 dated May 17, 2010.
International Search Report of Application No. PCT/IL04/00265 dated Aug. 26, 2004.
Office Action, issued Feb. 18, 2011, for U.S. Appl. No. 11/415,171.
Japanese Office Action, issued Dec. 7, 2010, for Japanese Application No. 2006-112106.
Office Action for U.S. Appl. No. 11/295,491 Dated Mar. 2, 2009.
Office Action issued for U.S. Appl. No. 11/295,491, dated Nov. 25, 2011.
Office Action issued for U.S. Appl. No. 11/976,794, dated Oct. 25, 2011.
Office Action of U.S. Appl. No. 13/906,140 dated Sep. 18, 2013.
Notice of Allowance issued by the United States Patent and Trademark Office for U.S. Appl. No. 13/906,140 dated Dec. 26, 2013.
Notice of Allowance issued for U.S. Appl. No. 11/976,794, dated Feb. 21, 2012.
Final Office Action issued for U.S. Appl. No. 11/295,491, dated Mar. 13, 2012.
Final Office Action from U.S. Appl. No. 11/415,171 dated Aug. 5, 2011.
Office Action from U.S. Appl. No. 11/295,491, dated Nov. 2, 2015.
"Wireless Transmission of a Colour Television Moving Image from the Stomach Using a Miniature CCD Camera, Light Source and Microwave Transmitter", CP Swain, et al., Gastrointestinal Endoscopy, vol. 45, No. 4 at 62 (1997).
"Imaging Device makes Chip-Sized Cameras a Real-World Possibility," Pollack, New York Times (May 27, 1997).
Final Office Action issued in U.S. Appl. No. 11/295,491 issued Feb. 11, 2016.

* cited by examiner

DEVICE AND SYSTEM FOR IN VIVO IMAGING

PRIOR APPLICATION DATA

This application is a continuation of prior application Ser. No. 09/800,470, filed on Mar. 8, 2001, now U.S. Pat. No. 7,009,634 entitled "A DEVICE AND SYSTEM FOR IN VIVO IMAGING" which in turn claims priority from prior U.S. provisional application 60/187,883, filed on Mar. 8, 2000, entitled "IN-VIVO IMAGING DEVICE AND SYSTEM", and is a continuation of prior application Ser. No. 11/295,491, filed Dec. 7, 2005, entitled "A DEVICE AND SYSTEM FOR IN VIVO IMAGING," all of which being incorporated by reference herein in their entirety.

FIELD OF THE INVENTION

The present invention relates to an in vivo imaging device and system such as for imaging the digestive tract.

BACKGROUND OF THE INVENTION

Among known in vivo measuring systems are endoscopes, which are often utilized to provide images of the upper or lower gastro-intestinal tract. However, endoscopes do not provide views of the entire length of the small intestines. Additionally, they are uncomfortable, may cause damage to the patient and are complex to operate.

Swallowable electronic capsules which are moved through the digestive tract through the action of digestion and which collect data and transmit the data to a receiver system are known, one such example is the "Heidelberg" capsule. Yet another example is a capsule disclosed in U.S. Pat. No. 5,604,531. These capsules may be utilized to measure pH, temperature and pressure throughout the intestines.

SUMMARY OF THE INVENTION

The device and system of the present invention enable obtaining in vivo images from within body lumens or cavities, such as images of the entire length of the gastro-intestinal (GI) tract. The device and system contain an imaging system that includes a complementary metal oxide semiconductor (CMOS) imaging camera. The device also contains an ultra low power radio frequency (RF) transmitter for transmitting signals from the CMOS imaging camera to a receiving system.

The CMOS imaging camera is an ultra low power imager, has low sensitivity to the red spectrum and is provided in chip scale packaging (CSP). The transmitter is an ultra low power RF transmitter with high bandwidth input, possibly provided in chip scale packaging.

The high integration and low power consumption achieved by the imaging system of the device and system of the invention were unobtainable prior to the advances in CMOS technology. Further, an ultra low power, high bandwidth input transmitter for video signals is unknown in the art. Also, an RF product in CSP has not been previously disclosed in the art.

Further, the imaging system may utilize a white light emitting diode (LED) as a light source rather than a reddish incandescence miniature bulb or an RGB LED presently used in the art. The white LED enables to produce a higher quality and more pleasant to the eye image.

There is therefore provided, in accordance with an embodiment of the invention, an in vivo imaging device. The device consists of at least one imaging system for producing video output, preferably digital output, and a transmitter which transmits the video output to a receiving system.

The imaging system includes a CMOS imaging camera, at least one illumination source for illuminating an in vivo site and an optical system for imaging the in vivo site onto the CMOS imaging camera.

The illumination source may be a white LED. The term "white LED" as referred to herein relates to a combination of a blue LED chip (emitting light in the blue spectrum range) and a refracting crystal. The blue LED chip is encapsulated within the refracting crystal such that blue light incident on the crystal is emitted in different spectrums, resulting in white light. The white light emitted from the refracting crystal has a small fraction of red light and an even smaller, almost nonexistent, fraction of infra red (IR) light.

The illumination source may be a specific integrated light source in which a refracting crystal matrix has a plurality of blue LED chips integrated therein.

The components of the device are harbored in a housing having an optical window. The housing is configured for being inserted and passing through body lumens or cavities.

Also provided, in accordance with an embodiment of the invention, is a system for in vivo imaging, which includes an imaging system producing video output, preferably digital output, a transmitter which transmits the video output of the imaging system and a receiving system for receiving the transmitted video output. The imaging system consists of a CMOS imaging camera, an illumination source for illuminating an in vivo site and an optical system for imaging the in vivo site onto the CMOS imaging camera.

The system may further comprise an antenna array capable of surrounding a body and comprising one or a plurality of antennas for receiving the transmitted video output and for producing a plurality of received signals. Also the system may include a demodulator capable of transforming the plurality of received video signals into a single video datastream. The system may also comprise a data processing system which generates tracking and video data from the single datastream.

The receiving system and data processor are typically located outside a patient.

Optionally, the system can also include an apparatus for operating the transmitter intermittently.

In one embodiment of the invention, the device is a swallowable capsule having an optical window and containing an imaging system for obtaining in vivo images of the entire length of the GI tract and a transmitter which transmits the obtained images to a receiving system.

The imaging system consists of a CMOS imaging camera, a white LED and a lens for imaging a GI tract site onto the CMOS imaging camera. The swallowable capsule also includes a contained energy source for providing energy the entirety of the electrical elements of the capsule.

Also provided in accordance with an embodiment of the invention is a transmitter for transmitting signals on RF to a receiving system. The transmitter, which is controlled by a normally opened (NO) switch, includes a control block for controlling the illumination and imager of the device of the invention.

The NO switch is controlled by an external magnet that keeps the switch closed while it is in proximity to the switch. However, an internal block maintains the logistics of an open switch, so as to keep the transmitter circuits and all capsule main subsystems inactive while the external magnet is present. Removal of the external magnet causes the switch to open and the internal block to close, thereby allowing the transmitter circuits and capsule main subsystems to be activated.

Further provided is a method for obtaining images in vivo. The method includes the steps of: illuminating a site in vivo; collecting remitted light onto pixels of a CMOS imaging camera, thereby generating an analog signal; processing and converting the analog signal to a digital signal; randomizing the digital signal; transmitting the digital signal to a receiving system; and processing the transmitted signals to obtain images of the in vivo site.

BRIEF DESCRIPTION OF THE DRAWINGS

The present invention will be understood and appreciated more fully from the following detailed description taken in conjunction with the drawings in which.

DETAILED DESCRIPTION OF THE INVENTION

The device and system of the invention are utilized for viewing inside body lumens and cavities and for transmitting at least video data.

Figure 1:
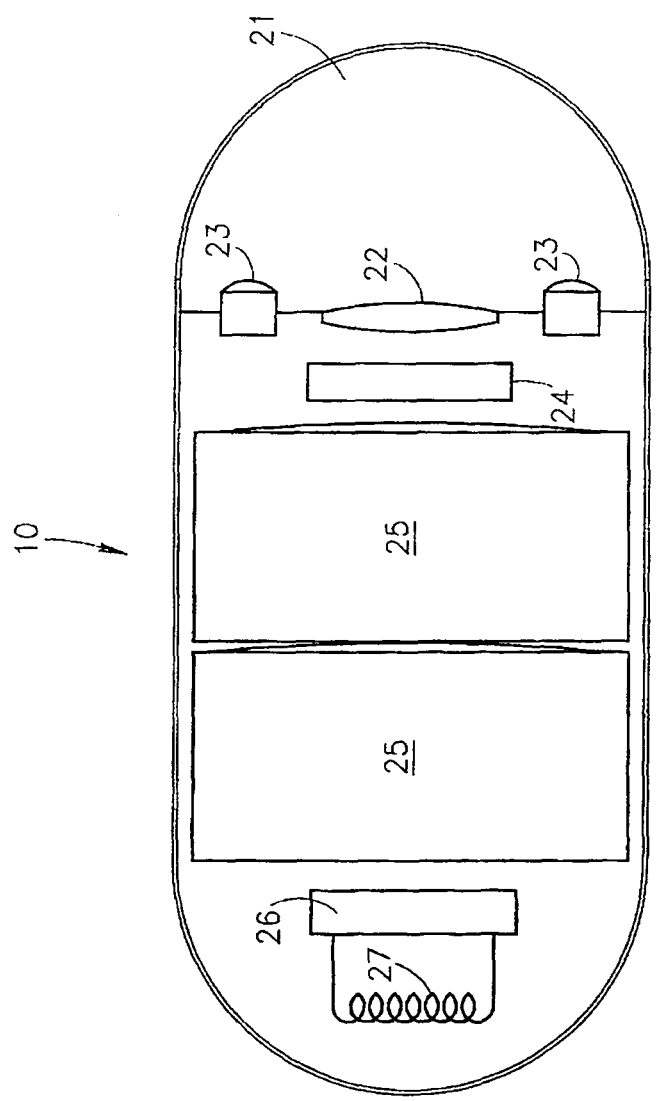
FIG. 1 is a schematic longitudinal cross section illustration of an in vivo imaging device according to an embodiment of the invention.

Reference is now made to FIG. 1 which illustrates the device and its components, according to an embodiment of the invention. The device 10 typically comprises an optical window 21 and an imaging system for obtaining images from inside a body lumen, such as the GI tract. The imaging system includes an illumination source 23, such as a white LED, a CMOS imaging camera 24, which detects the images and an optical system 22 which focuses the images onto the CMOS imaging camera 24. The illumination source 23 illuminates the inner portions of the body lumen through optical window 21. Device 10 further includes a transmitter 26 and an antenna 27 for transmitting the video signal of the CMOS imaging camera 24, and a power source 25, such as a silver oxide battery, that provides power to the electrical elements of the device 10.

It will be appreciated that a plurality of CMOS imaging cameras may be used in the device and system of the invention. Each CMOS imaging camera may include its own optical system and either one or more illumination sources, in accordance with specific requirements of the device or system.

Images obtained by the CMOS camera 24 are transmitted to a receiving system (not shown), which may also include a data processing unit. The receiving system and data processing unit are typically located outside a patient.

The device 10 is capsule shaped, can be easily swallowed and may passively pass through the entire GI tract, pushed along by natural peristalsis.

Nonetheless, it should be appreciated that the device may be of any shape suitable for being inserted into and passing through a body lumen or cavity. Furthermore, the device of the invention may be attached or affixed on to an instrument that is inserted into body lumens and cavities, such as on an endoscope, laparoscope, stent, needle, catheter etc.

Thus, the device may be introduced into a body lumen or cavity by swallowing, by using an endoscopic device, by surgery and so on.

A suitable CMOS imaging camera 24 is, for example, a "camera on a chip" type CMOS imager specified by Given Imaging Ltd. of Yokneam, Israel and designed by Photobit Corporation of California, USA, with integrated active pixel and post processing circuitry (as will be further described with reference to FIG. 2). The single chip camera can provide either black and white or color signals.

The CMOS imaging camera 24 is designed such that it is less sensitive to light in the red spectrum than known CMOS cameras.

The optical system 22 comprises at least one lens and optionally mirrors and/or prisms for collecting and collimating remitted light on to the pixels of the CMOS imaging camera 24. Typically, the optical system comprises an aspherical focussing lens. A suitable lens is, for example, the lens designed by Given Imaging Ltd. of Yokneam, Israel, in accordance with specific object plane, distortion and resolution parameters.

Illumination source 23, transmits illumination to the walls of the body lumen via the optical window 21. The lens of the optical system 22 then focuses remittent light onto the pixels of the CMOS imaging camera 24.

A single or plurality of light sources or a specific integrated light source may be used and positioned in accordance with specific imaging requirements, such as to avoid stray light etc. Also, the optical window 21 may be positioned and shaped according to the device shape and according to specific imaging requirements. For example, optimized imaging conditions can be obtained when optical window 21 is formed to define an ellipsoid shaped dome and the CMOS imaging chip camera system 24 and illumination sources 23 are positioned in the proximity of the focal plane of the shape defined by the optical dome. Obtaining the above imaging conditions is described in WO 00/76391, which is assigned to the common assignees of the present invention and which is hereby incorporated in its entirety by reference.

The in vivo sites imaged in the present invention are usually very close to the imager. For example, an 11×30 mm capsule passing through and imaging the small intestine, images the intestine walls from a very short distance. It is therefore possible to satisfy the illumination requirements of the imaging process utilizing solid state illumination sources, such as LEDs.

In an embodiment of the invention the illumination source is a white LED. The white light emitted from the white LED has a small fraction of red light and even smaller fraction of IR light. Hence, a white LED is beneficial for use with silicone based image sensors (such as CMOS imaging cameras) because of the silicone sensitivity to red and IR light.

In a system which includes the CMOS imaging camera of the invention with its reduced sensitivity to light in the red spectrum and a white LED illumination source, no IR reject filters (photopic filters) are needed.

A suitable transmitter may comprise a modulator which receives the video signal (either digital or analog) from the CMOS imaging camera, a radio frequency (RF) amplifier, an impedance matcher and an antenna. The transmitter will be further illustrated in FIG. 4.

Other optional parts of the system as well as the method for localization of a capsule containing the system within the digestive system may be similar to those described in U.S. Pat. No. 5,604,531 (which is assigned to the common assignees of the present invention and which is hereby incorporated in its entirety by reference).

Device 10 can additionally include sensor elements for measuring pH, temperature, pressure, etc. These sensor elements, some of which are described in the prior art, may be any element suitable for measuring conditions prevailing in the body lumen (for example, the digestive system) and that are capable of being appended to or included in the device.

Figure 2:
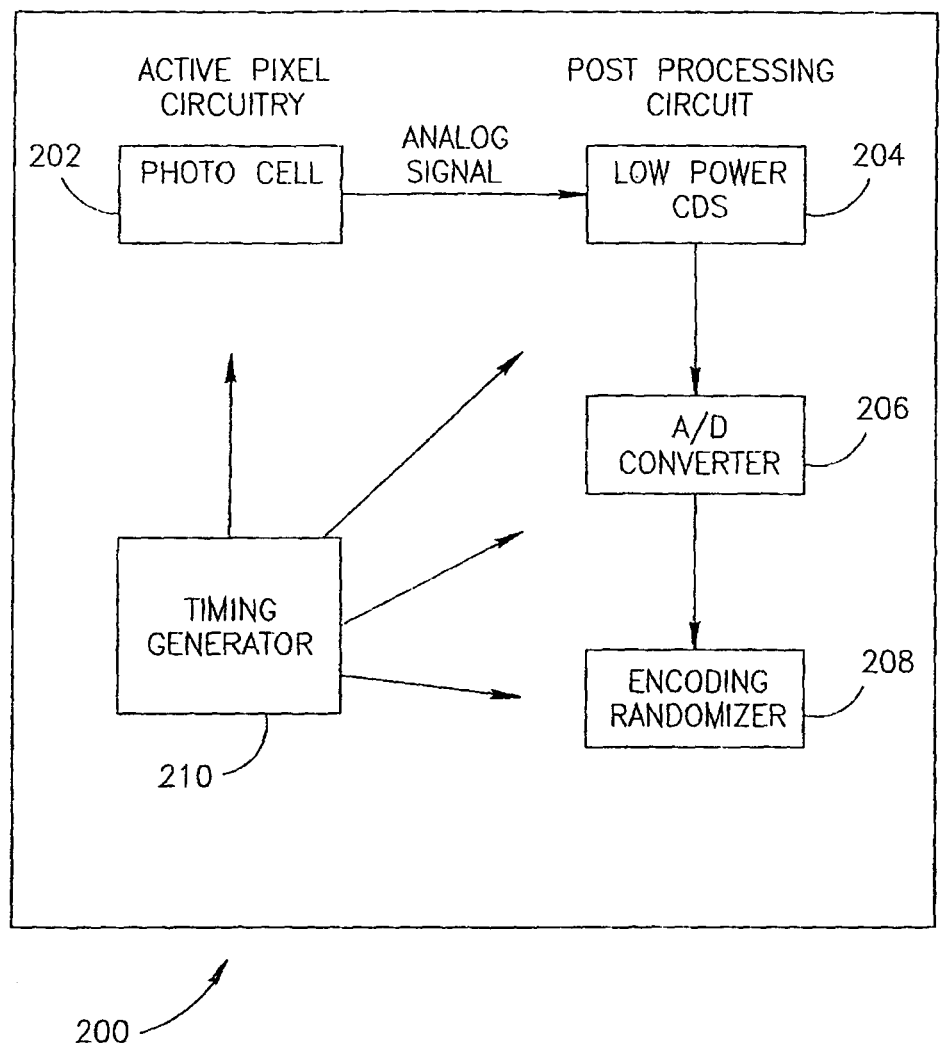
FIG. 2 is a schematic presentation of the CMOS imaging camera according to an embodiment of the invention.

Reference is now made to FIG. 2, in which a schematic layout of the CMOS imaging camera is presented. The CMOS imaging camera 200 comprises active pixel and post processing circuitry on a single chip. The CMOS imaging camera 200 includes photo cell 202 (the pixels of the CMOS imaging camera), correlated double sampler (CDS) 204, analog to digital (A/D) converter 206, encoding and randomizing unit 208 and timing generator 210 for control and synchronization of the circuitry elements.

Light collected by an optical system is directed onto CMOS imaging camera 200 and photons are converted to electrons as the light is absorbed by photo cell 202. Electrons are converted to electrical current and an analog signal is produced by the active pixel circuitry. The analog signal is conveyed for further processing by on-chip post processing circuitry. The signal is further processed by CDS 204. CDS 204 performs correlated double sampling, for canceling noise and signal shaping before conveying the signal to the A/D converter 206. The A/D converter 206 is a serial output A/D converted which enables serial, low power transmission of signals. The signal is converted into a digital signal and is further conveyed to encoding and randomizing unit 208 for defining frame and row parameters (encoding) and for priming the signals for transmission (randomizing). The encoding and randomizing unit 208 randomizes the occurrence of the digital "0" and "1" signals such that transmission is not impeded by a reoccurring signal of one type.

The CMOS imaging camera 200 is specified by Given Imaging Ltd. of Yokneam, Israel and designed by Photobit Corporation of California, USA, according to a specification adjusted to in vivo imaging. The CMOS imaging chip has ultra low power requirements (less than 3 milliwatts). The dynamics of the increase of dark current generated by the imaging camera, as a function of temperature, is less than that of solid state devices known in the art, such that at 37° C. a low fraction of the output video signal is dark current. Further, as discussed above, the imaging camera has reduced sensitivity to light in the red spectrum, abating the need for photopic filters.

Figure 3:
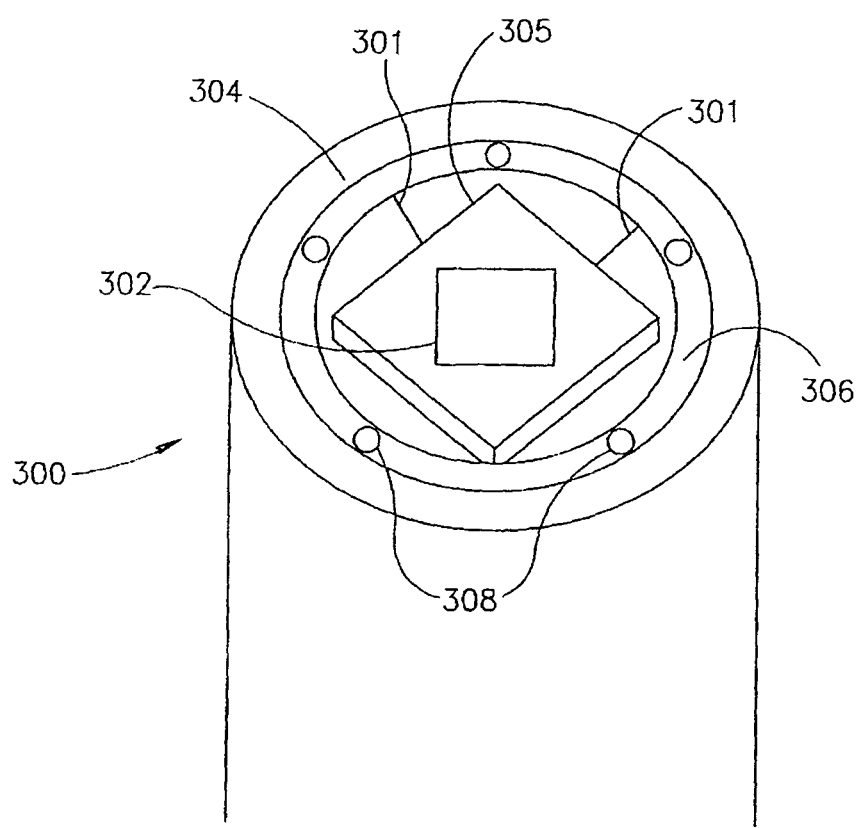
FIG. 3 is a cross section schematic illustration of a device, in accordance with an embodiment of the invention, including a specific integrated illumination source.

Reference is now made to FIG. 3 in which a device for in vivo imaging comprising a specific integrated light source is illustrated. Device 300 comprises CMOS imaging camera 302, an optical system (not shown) for imaging in vivo images onto the CMOS imaging camera 302 and an integrated light source 304 for illuminating a site in vivo. The device 300 further includes a transmitter 305 for transmitting video data from the imaging camera 302 to a receiver (not shown). The transmitter 305 generates a high voltage and current source for the light source 304. The integrated light source 304 is connected to the transmitter 305 through connective wires 301. The electrical components of the device are powered by a battery contained within the device (not shown).

The integrated light source 304 comprises a strip 306 of a refracting crystal matrix encircling the CMOS imaging camera 302. Blue LED chips 308, encapsulated within the refracting crystal matrix of strip 306, are positioned along the strip 306 such that illumination is provided in a ring around the CMOS imaging camera 302.

Blue LED chips 308 can also be sprinkled throughout the strip 306 such that the whole strip 306 emits light.

Figure 4:
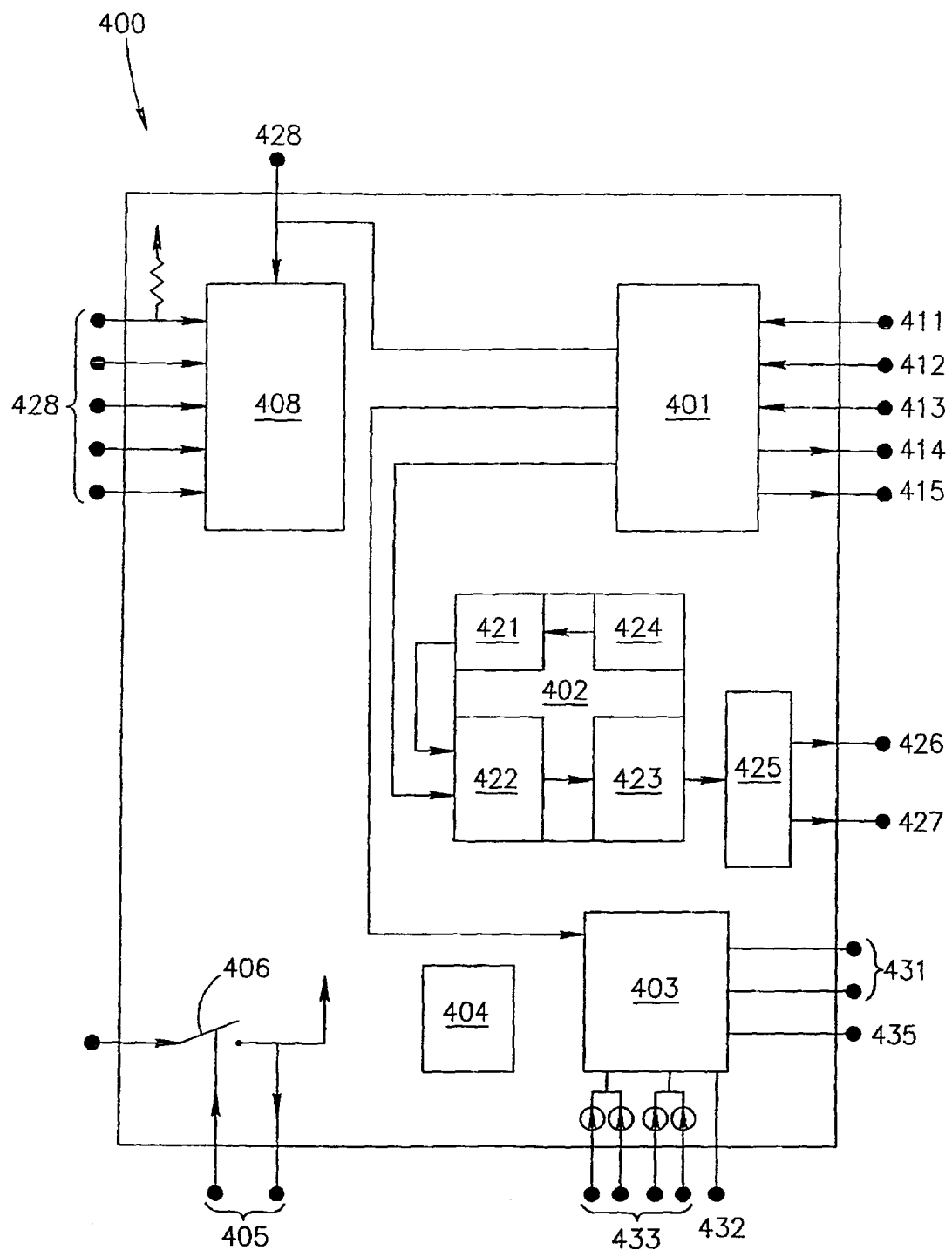
FIG. 4 is a block diagram of the transmitter in accordance with an embodiment of the invention.

Reference is now made to FIG. 4 in which a block diagram of the transmitter is illustrated. The transmitter 400, an ASIC (application specific integrated circuit) designed to fulfill international communication standards (such as the FCC) standards, operates on a minimum shift keying (MSK) modulation system to effect transmitting of digital signals through antenna 426 and 427 on radio frequencies to a receiving system. The transmitter 400 also controls the illumination and imager of the device of the invention and the logical conversion of the switch (as described above). The transmitter 400 includes a one time programming unit 408 in communication with external programming input 428, a control logic block 401 for communicating with the imager, a phase lock loop (PLL) 402 in communication with modulator 425, optionally, a LED power and control block 403 for controlling the illumination, a main oscillator 404 and a switch 405 which controls an internal electronic switch 406.

The control logic block 401 communicates with the imager, reads preprogrammed parameters and performs the interface to the "outside" world in the programming mode. Control logic block 401 maintains a master clock, is synchronized by bit rate data 412 and frame rate 413, and through control 411, which is generated by the imager, triggers LED power and control block 403. Control logic block 401 further controls the master clock 414 and the imager shutdown 415.

During shutdown the transmitter sends out beacon signals only. The shutdown enables economic use of the device's power supply. For example, in a device designed for imaging the small intestine, the transmitter 400 may be programmed to include a two hour delay, during which period shutdown of the imager and other device electronics is effected. Two hours is approximately the time it takes a swallowable device to pass the stomach and enter the small intestine, in particular patients. Thus, in those patients, the device will utilize power from the battery, for collecting images, only when the device has reached the small intestine.

The PLL 402 is a feedback system intended to automatically correct drifts in the transmitted frequency. PLL 402 includes a pre-scaler 424 for fast frequency dividing that is not dependant on the channel frequency. The pre-scaler 424 is in communication with a divider 421 that divides the frequency of the oscillator 404 to perform the reference frequency for the PLL. The division value is channel dependant. The PLL 402 also includes a phase frequency detector (PFD) 422 for performing the frequency comparison and the phase comparison of the PLL, and a charge pump 423 for performing the shape of the loop transmission of the whole loop.

LED power and control block 403 includes a high voltage source 432 that is controlled by the external capacitor 431. LED power and control block 403 also includes a high current source 433 and the peak current value of the LEDs is controlled by the resistor which is connected to LedRes 435.

The transmitter 400 is controlled by an external magnetic switch 405. The switch 405 is a normally opened (NO) switch that is kept closed by an external magnet, as described above. Switch 405 controls an internal electronic switch 406 that controls all the device electronics. Electronic switch 406 includes a low leakage circuitry to convert the logic of the NO switch 405 to "normally closed" (NC) logic, such that although switch 405 is a NO switch it will keep the transmitter inactive while it is closed.

The low leakage circuit only uses 1%-3% of the battery power per year, so that the internal electronic switch 406 is not a significant factor in the power regimen of the device.

In an embodiment of the invention the device is a swallowable capsule having an optical window and comprising a CMOS imaging camera, white LEDs, an optical system, a transmitter and battery. The swallowable capsule is kept inactive while contained in a package having a magnet, such as the magnetic packaging described in PCT application IL00/00752 (which is assigned to the common assignee of the present invention and which is hereby incorporated in its entirety by reference). Just prior to use the package having the magnet is removed enabling the switch 405 to be opened, thereby activating the transmitter and with it, initiating imager and illumination operation.

The input bandwidth of the information in the transmitter 400 is over 1.35 Megabit per second. Such a low powered high input bandwidth transmitter for transmitting video data, has not yet been shown in the art.

Figure 5:
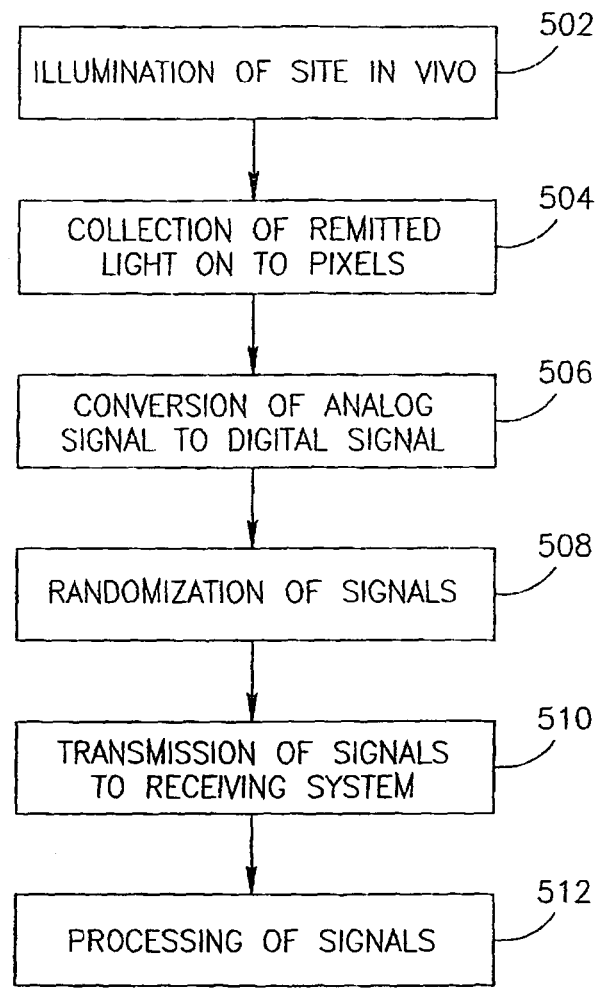
FIG. 5 is a block diagram presentation of the method according to an embodiment of the invention.

Reference is now made to FIG. 5 in which a block diagram of the method of the invention is illustrated. The method for in vivo imaging includes the following steps: illuminating a site in vivo (502); collecting remitted light onto pixels of a CMOS imaging camera, thereby generating an analog signal (504); converting the analog signal to a digital signal (506); randomizing the digital signal (508); transmitting the digital signal to a receiving system (510) and processing the transmitted signals to obtain images of the in vivo site (512).

The step of illumination (502) is preferably carried out by employing white LEDs to illuminate the site in vivo. Illumination may be continuous or alternating in accordance with specific requirements of the system.

Collecting light remitted from the site in vivo (504) and directing it on to the pixels of a CMOS imaging chip is achieved by employing an optical system which comprises a lens and which may further comprise any suitable collimator.

Conversion of the analog signal to a digital signal (506) is preferably effected in a serial manner.

Randomizing the digital signal (508), namely randomizing the occurrence of the digital signals ("0" and "1"), is performed so that transmission is not impeded by a reoccurring signal of one type.

Transmission of the signal (510) is accomplished using radio frequencies (approximately 432-434 Mhz) at a rate of two to eight frames per second to an array of antennas attached to a patient's body. The antennas allow image capture and are also used to calculate and indicate the position of the imager in the patient's body. An example of the calculation and indication the position of the imager in the patient's body is provided in the above mentioned U.S. Pat. No. 5,604,531.

Processing of signals (512) can be carried out by employing suitable processors and software. For example, the RAPID software (propriety software developed and owned by Given Imaging Ltd. of Yokneam, Israel) is used to obtain a video clip of images captured from within the GI tract. The video clip can be synchronized with the trajectory of the imaging device as it passes through the GI tract to enable localization of the device in the GI tract.

Additionally, a plurality of receiving antennas can be used which can be moved to the location enabling best receiving conditions.

The images can be stored on a small portable recorder carried on a belt and subsequently downloaded for analysis and retrieval. Additionally, the receiver can be connected directly to a stationary data recorder.

Experiments were carried out with an 11×30 mm capsule comprising a CMOS imaging chip and miniature processor, white LED light sources, a short focal length lens and a miniature transmitter and antenna. The capsule, powered by silver oxide batteries, was swallowed and more than 5 hours of continuous recording of images from the gastrointestinal tract were achieved.

Live transmission of good quality video images were obtained for up to 6 hour periods in ambulatory dogs.

With ethical committee approval a human volunteer study was performed. The capsule was easily swallowed. Moving images were obtained from the stomach and small intestine. No discomfort was experienced. The optical window remained clear throughout the whole transmission.

Trigonometric analysis of signal strength allowed continuous monitoring of the capsule position. Imaging of the small bowl was successfully completed in 2 hours.

It will be appreciated by persons skilled in the art that the present invention is not limited to what has been particularly shown and described hereinabove. Rather the scope of the present invention is defined only by the claims which follow:

The invention claimed is:

1. A swallowable capsule for in vivo imaging of the gastrointestinal tract, said capsule comprising a housing, including a single uninterrupted transparent dome shaped optical window, the housing enclosing at least:
   an imaging camera;
   a plurality of illumination sources for emitting light to a gastrointestinal tract site from the base of the single uninterrupted transparent dome shaped optical window;
   a lens for receiving at the base of the single uninterrupted transparent dome shaped optical window light reflected from the gastrointestinal tract site onto the imaging camera, the lens and the illumination sources being separated from the single uninterrupted transparent dome shaped optical window, the imaging camera imaging the site via the single uninterrupted transparent dome shaped optical window and via the lens, and the illumination sources illuminating the site directly via the single uninterrupted transparent dome shaped optical window and not via the lens; and
   a transmitter for transmitting an output of the imaging camera.

2. The swallowable capsule of claim 1, wherein the imaging camera comprises a CMOS imaging camera.

3. The swallowable capsule according to claim 2 wherein the CMOS imaging camera comprises active pixel circuitry.

4. The swallowable capsule according to claim 2 wherein the CMOS imaging camera comprises a correlated double sampler for processing an analog signal produced by the active pixel circuitry.

5. The swallowable capsule according to claim 2 wherein the CMOS imaging camera comprises an analog to digital converter having serial output.

6. The swallowable capsule according to claim 2 wherein the CMOS imaging camera comprises an encoding and randomizing unit for defining frame and row parameters and for priming digital signals for transmission.

7. The swallowable capsule according to claim 2 wherein the CMOS imaging camera comprises:
- active pixel circuitry, said circuitry producing an analog signal;
- a correlated double sampler for processing the analog signal produced by the active pixel circuitry;
- an analog to digital converter having serial output for converting the analog signal to a digital signal; and
- an encoding and randomizing unit for defining frame and row parameters and for priming the digital signal for transmission.

8. The swallowable capsule according to claim 1 wherein the illumination sources include white LEDs.

9. The swallowable capsule according to claim 1 wherein the illumination sources comprise a refracting crystal matrix having at least one blue LED chip integrated therein.

10. The swallowable capsule according to claim 1 wherein the lens comprises an aspherical focussing lens.

11. The swallowable capsule according to claim 1 wherein the lens comprises at least one collimator for collecting remittent light.

12. The swallowable capsule according to claim 1 wherein the transmitter comprises an internal electronic switch for converting a logic of a normally open switch to a normally closed logic.

13. The swallowable capsule according to claim 1 wherein the transmitter comprises a control block for controlling the imaging camera.

14. The swallowable capsule according to claim 13 wherein the control block is to control the illumination sources.

15. The swallowable capsule according to claim 13 wherein the control block is to send a shutdown signal to the imaging camera to inactivate the imaging camera and to the transmitter to inactivate main capsule subsystems.

16. The swallowable capsule according to claim 1 wherein a shutdown signal is sent from a control block for a period following activation of the capsule.

17. The capsule of claim 1, wherein the lens and imaging camera are aligned along a longitudinal axis of the capsule.

18. The capsule of claim 1, wherein the dome shaped optical window is aligned along a longitudinal axis of the capsule.

19. The capsule of claim 1, wherein the illumination sources are positioned in the proximity of the focal plane of the shape defined by the dome shaped optical window.

* * * * *